(12) United States Patent
Young

(10) Patent No.: US 7,011,658 B2
(45) Date of Patent: Mar. 14, 2006

(54) DEVICES AND METHODS FOR SPINAL COMPRESSION AND DISTRACTION

(75) Inventor: John Stewart Young, Memphis, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 414 days.

(21) Appl. No.: 10/092,961

(22) Filed: Mar. 4, 2002

(65) Prior Publication Data

US 2003/0167059 A1    Sep. 4, 2003

(51) Int. Cl.
A61B 17/56 (2006.01)
A61F 2/00 (2006.01)
A61F 2/30 (2006.01)

(52) U.S. Cl. ............................... 606/61; 606/90
(58) Field of Classification Search ............... 606/53, 606/54, 57, 60, 61, 86, 105, 58, 87, 90
See application file for complete search history.

(56) References Cited

U.S. PATENT DOCUMENTS

| 2,333,033 | A |   | 10/1943 | Mraz |
|-----------|---|---|---------|------|
| 4,034,746 | A | * | 7/1977  | Williams .................. 600/217 |
| 4,926,849 | A | * | 5/1990  | Downey .................... 602/34 |
| 5,167,662 | A |   | 12/1992 | Hayes et al. |
| 5,290,312 | A |   | 3/1994  | Kojimoto et al. |
| 5,439,463 | A |   | 8/1995  | Lin |
| 5,443,515 | A |   | 8/1995  | Cohen et al. |
| 5,540,687 | A |   | 7/1996  | Fairley et al. |
| 5,540,696 | A | * | 7/1996  | Booth et al. .................. 606/88 |
| 5,700,263 | A |   | 12/1997 | Schendel |
| 5,871,487 | A | * | 2/1999  | Warner et al. ............... 606/130 |
| 5,911,723 | A | * | 6/1999  | Ashby et al. ................. 606/88 |
| 5,928,231 | A | * | 7/1999  | Klein et al. .................. 606/60 |
| 6,113,600 | A |   | 9/2000  | Drummond et al. |
| 6,126,660 | A |   | 10/2000 | Dietz |
| 6,193,721 | B1 | * | 2/2001  | Michelson .................... 606/70 |
| 6,260,737 | B1 | * | 7/2001  | Gruendeman .............. 222/391 |
| 6,332,887 | B1 | * | 12/2001 | Knox ........................ 606/87 |
| 6,648,891 | B1 | * | 11/2003 | Kim .......................... 606/69 |

* cited by examiner

Primary Examiner—Eduardo C. Robert
Assistant Examiner—Anu Ramana
(74) Attorney, Agent, or Firm—Krieg Devault LLP

(57) ABSTRACT

A device for applying a corrective force to a spinal column segment is provided that includes a mechanism with opposite first and second engagement ends and driving means for moving the opposite engagement ends in extension and retraction directions. A locking mechanism has a first position in engagement with the mechanism to prevent the opposite engagement ends from being moved in one of the extension and retraction directions while allowing movement in the other of the extension and retraction directions. The locking mechanism has a second position that allows the opposite engagement ends to be moved in both of the extension and retraction directions. The locking mechanism can also be configured to prevent the opposite engagement ends from being moved in either of the extension and retraction directions when in the first position.

41 Claims, 8 Drawing Sheets

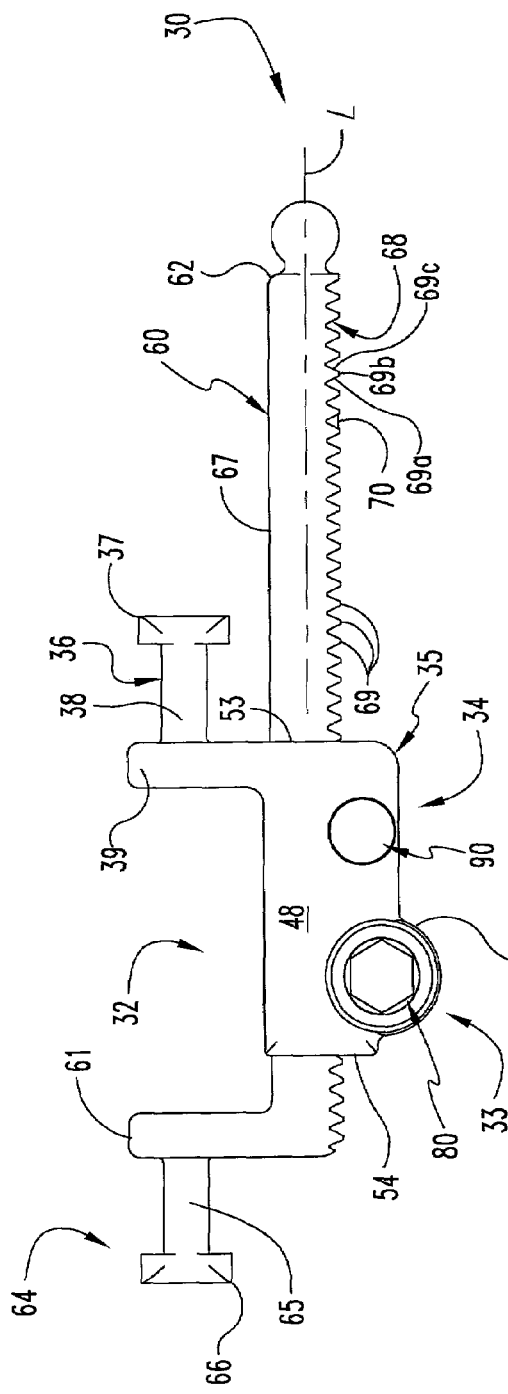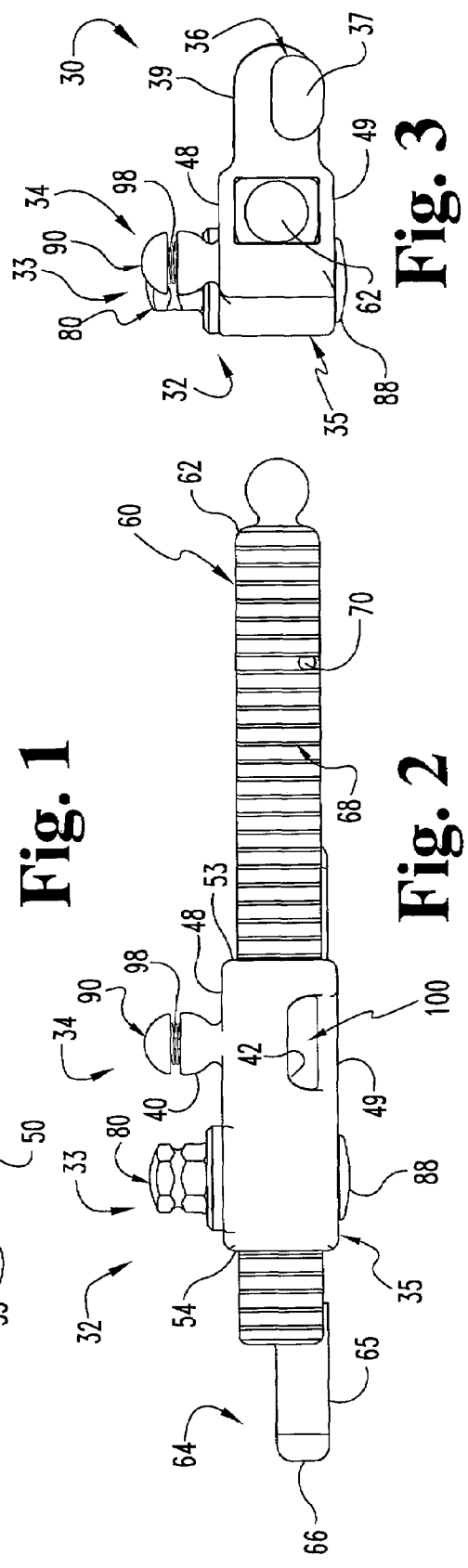

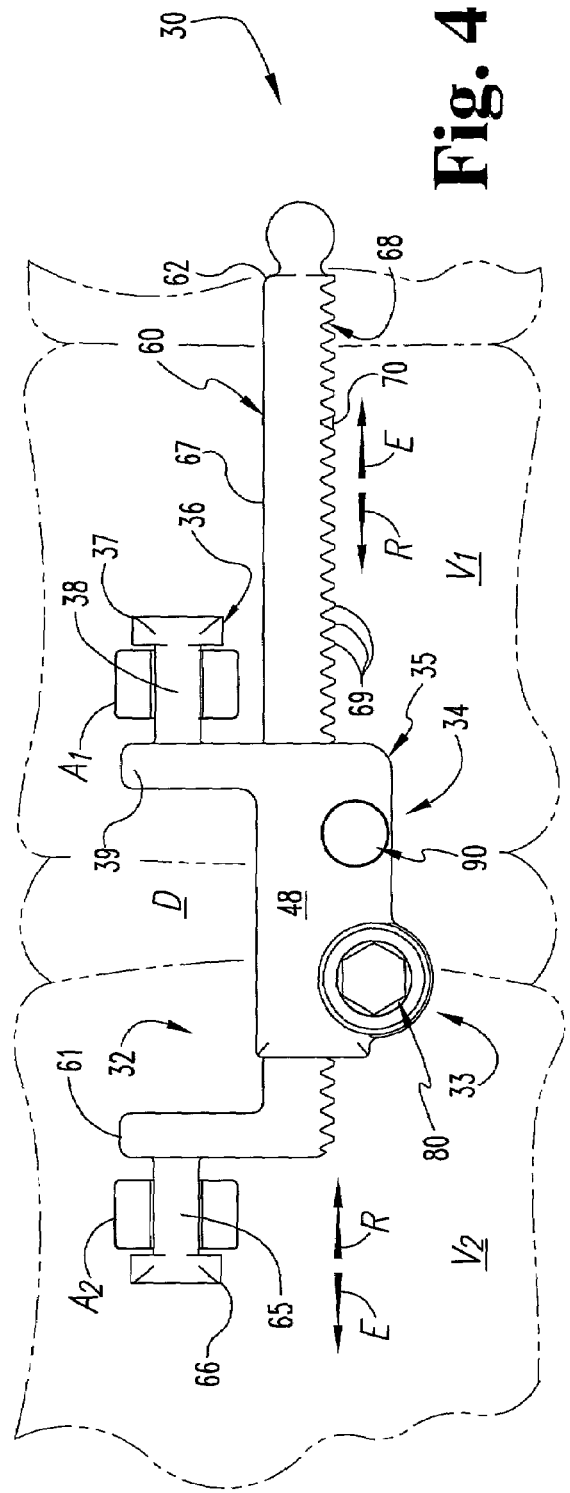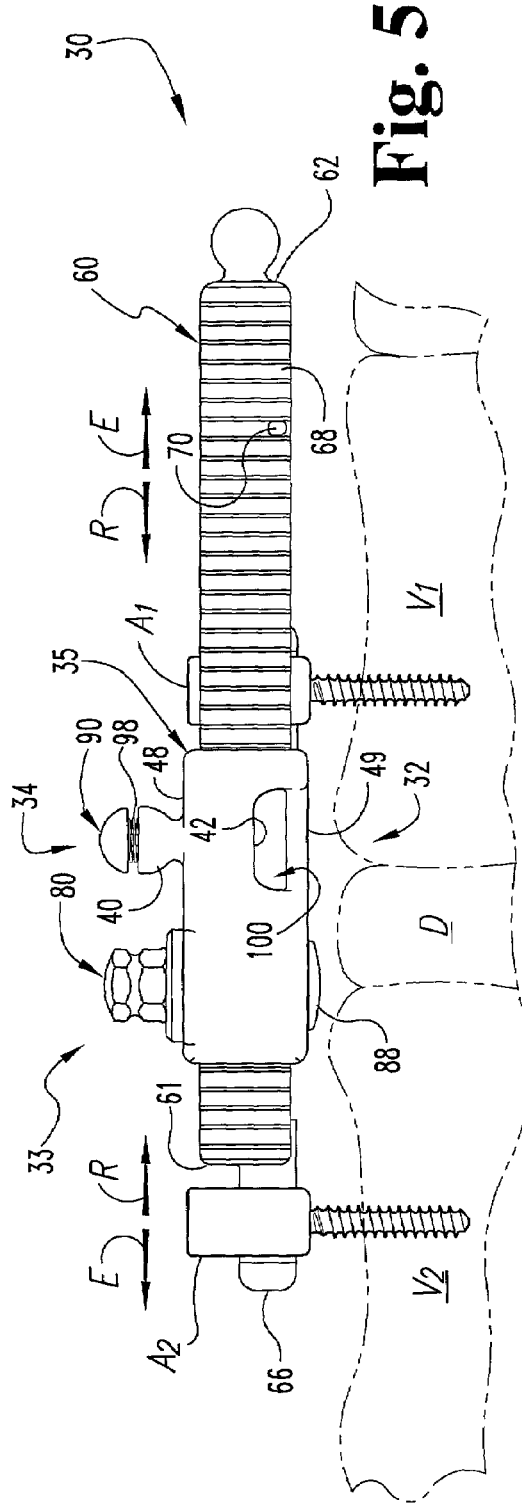

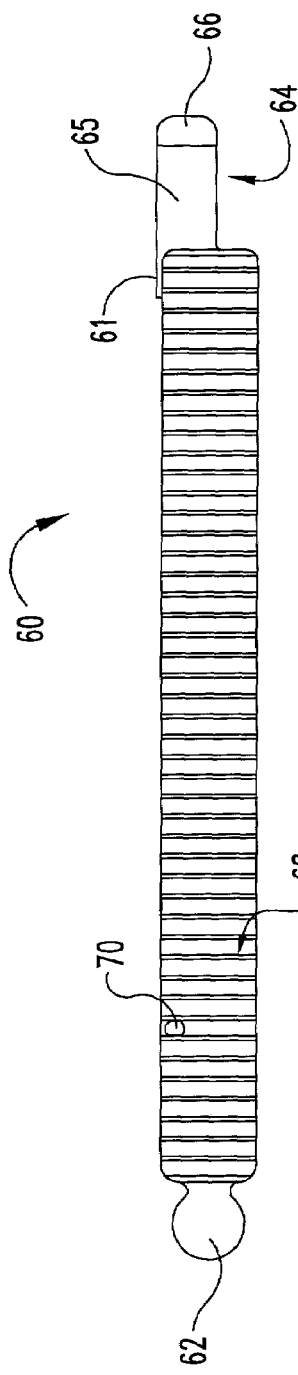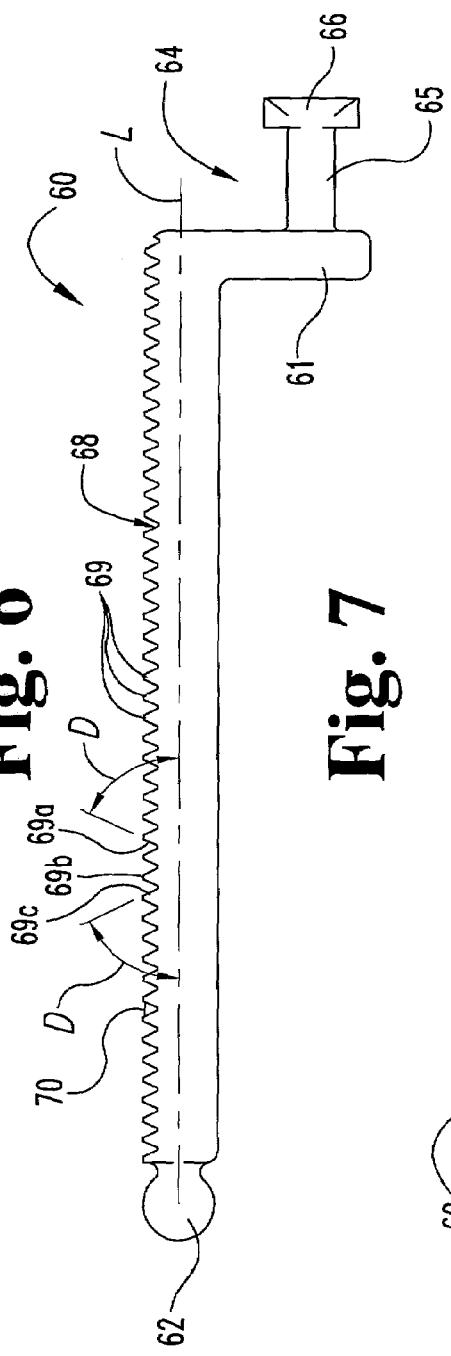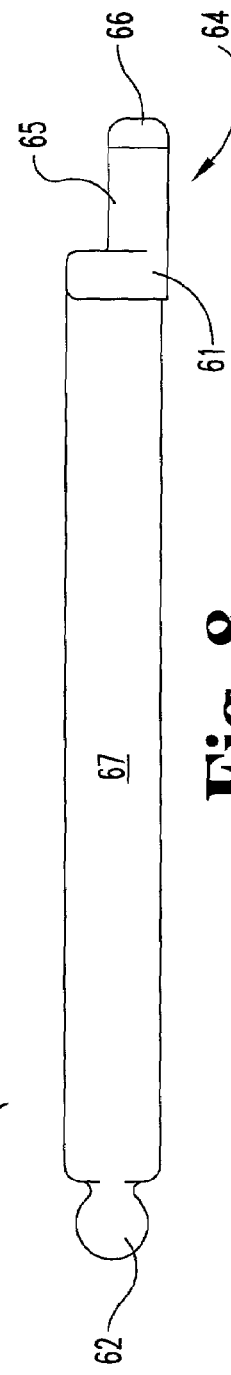

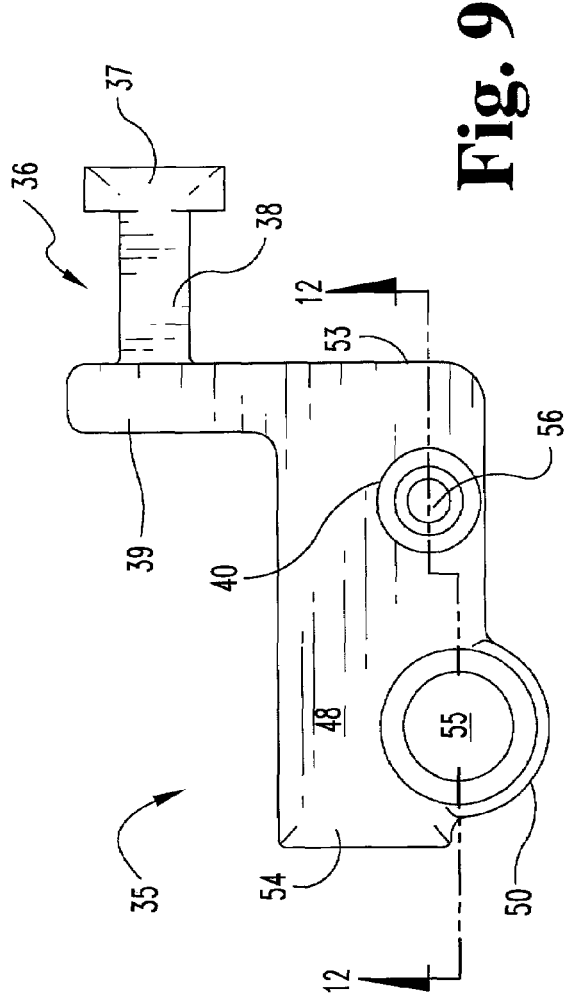
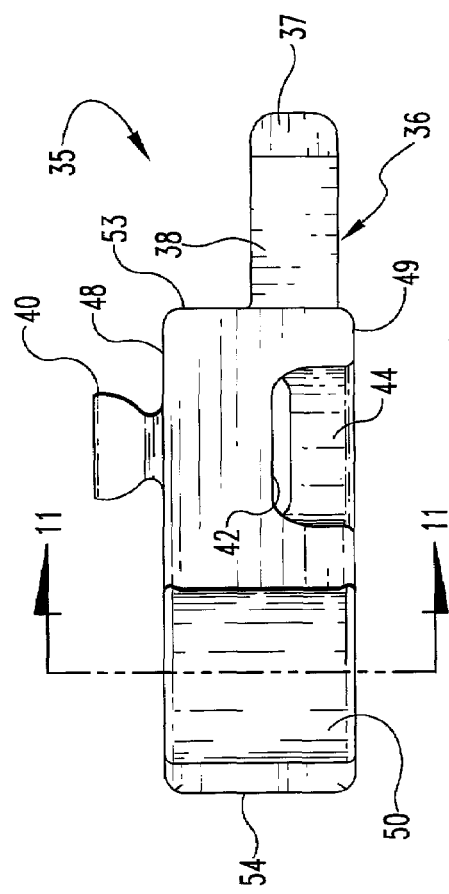
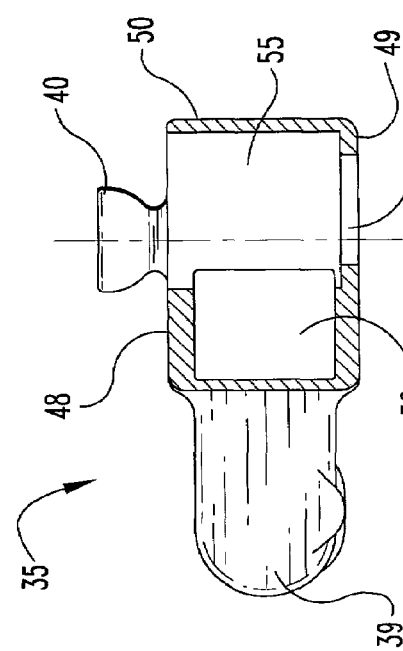
Fig. 9
Fig. 10
Fig. 11

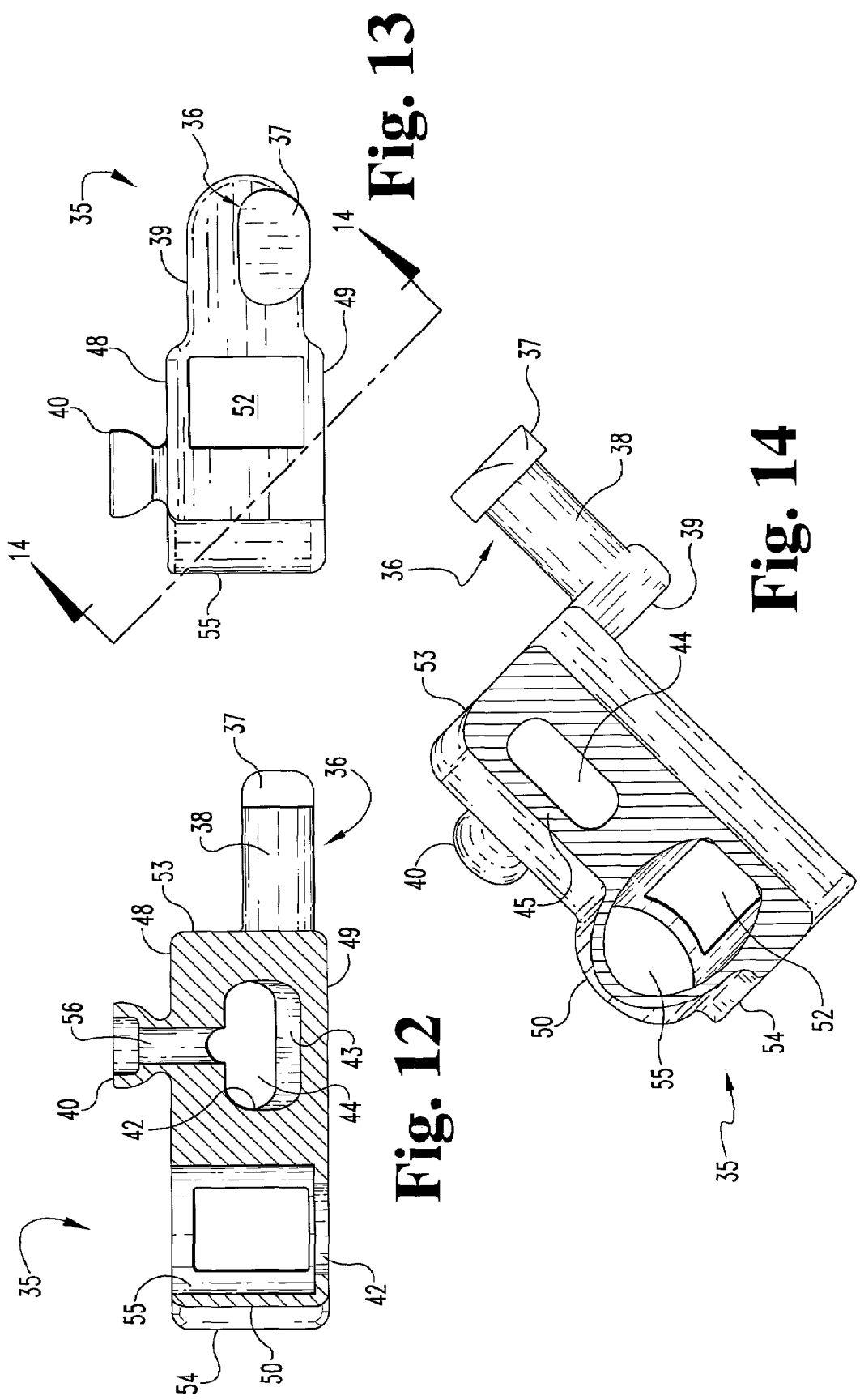

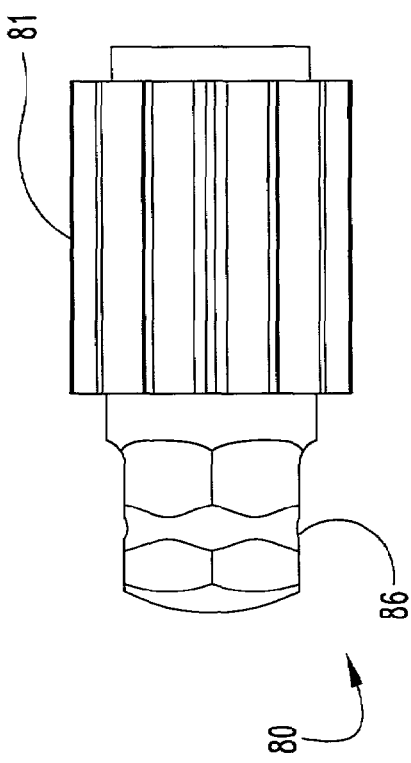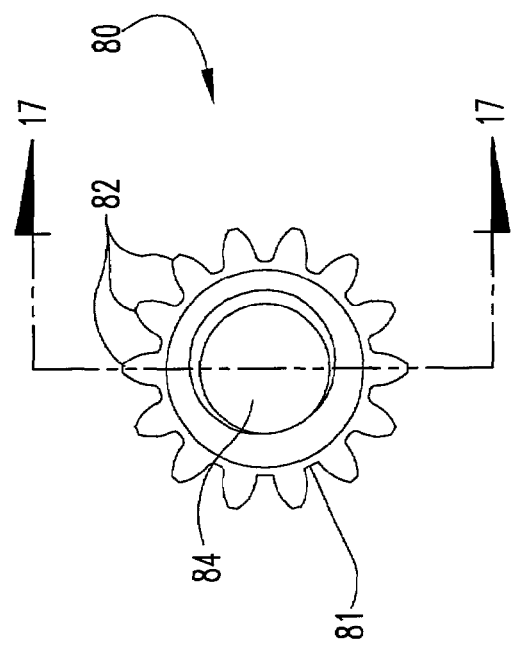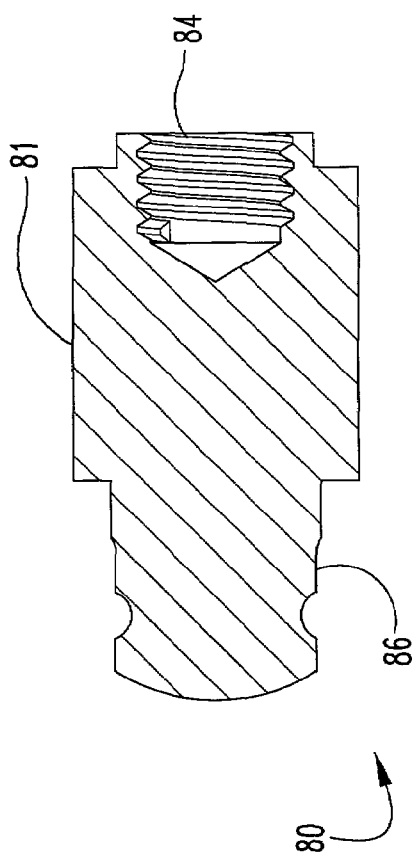

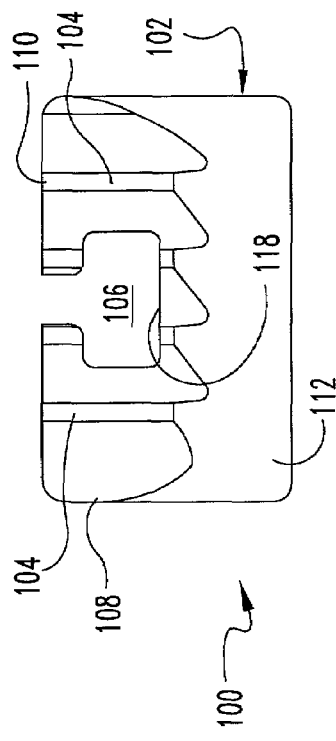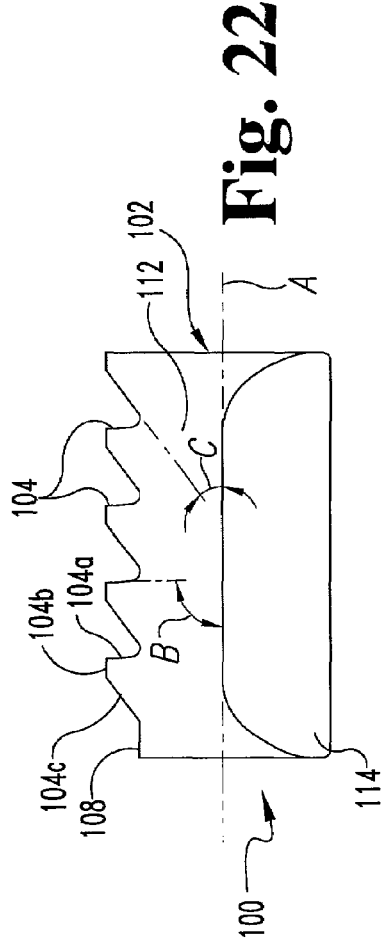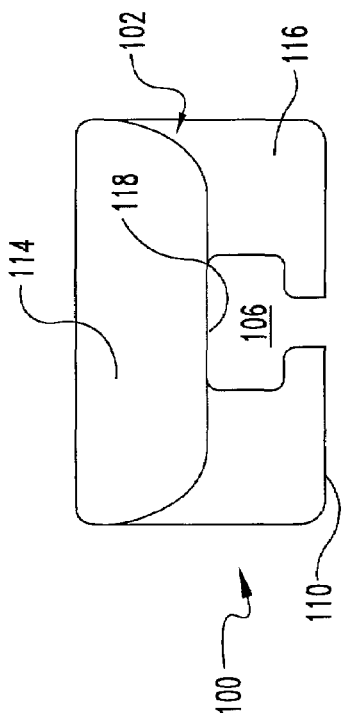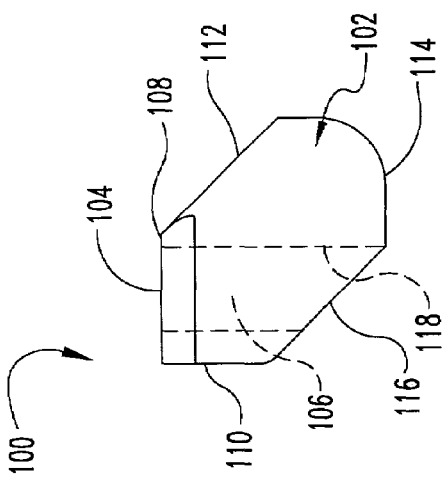

DEVICES AND METHODS FOR SPINAL COMPRESSION AND DISTRACTION

FIELD OF THE INVENTION

The present invention relates to surgical methods and devices for spinal surgery, and in particular to devices and methods for applying compression and/or distraction forces to the spine.

BACKGROUND OF THE INVENTION

In many surgical spinal procedures, such as, for example, the correction of scoliosis, nerve root decompression, interbody fusion, repair of kyphosis and treatment of other spinal defects or trauma, it is desirable or necessary to supply forces by compression and/or distraction in the defective region. While there are devices that exist for applying forces to the spine, there remains a need for devices and methods that improve surgeon efficiency and provide the surgeon additional options in the application of such forces. The present invention is directed toward meeting these needs, among others.

BRIEF DESCRIPTION OF THE DRAWINGS

FIG. 1 is an elevation view showing one side of a device according to the present invention.

FIG. 2 is an elevation view of another side of the device of FIG. 1

FIG. 3 is an end view of the device of FIG. 1.

FIG. 4 illustrates the device in its FIG. 1 orientation secured to a portion of the spinal column.

FIG. 5 illustrates the device in its FIG. 2 orientation secured to a portion of the spinal column.

FIG. 6 is an elevation view of one side of a rack comprising a portion of the device of FIG. 1.

FIG. 7 is an elevation view of another side of the rack of FIG. 6.

FIG. 8 is an elevation view of yet another side of the rack of FIG. 6.

FIG. 9 is an elevation view of one side of a body comprising a portion of the device of FIG. 1.

FIG. 10 is an elevation view of another side of the body of FIG. 9.

FIG. 11 is a section view of the body through line 11—11 of FIG. 10.

FIG. 12 is a section view of the body through line 12—12 of FIG. 9.

FIG. 13 is a right hand end view of the body of FIG. 9.

FIG. 14 is a section view of the body through line 14—14 of FIG. 13.

FIG. 15 is an elevation view of a pinion comprising a portion of the device of FIG. 1.

FIG. 16 is an end view of the pinion of FIG. 15.

FIG. 17 is a section view through line 17—17 of FIG. 16.

FIG. 20 is an end view of a lock member comprising a portion of the device of FIG. 1.

FIG. 21 is an elevation view in the direction of the top of the lock member of FIG. 20.

FIG. 22 is an elevation view of the right hand side of the lock member of FIG. 20.

FIG. 23 is an elevation view of the bottom of the lock member of FIG. 20.

DESCRIPTION OF THE ILLUSTRATED EMBODIMENT

Figure 18:
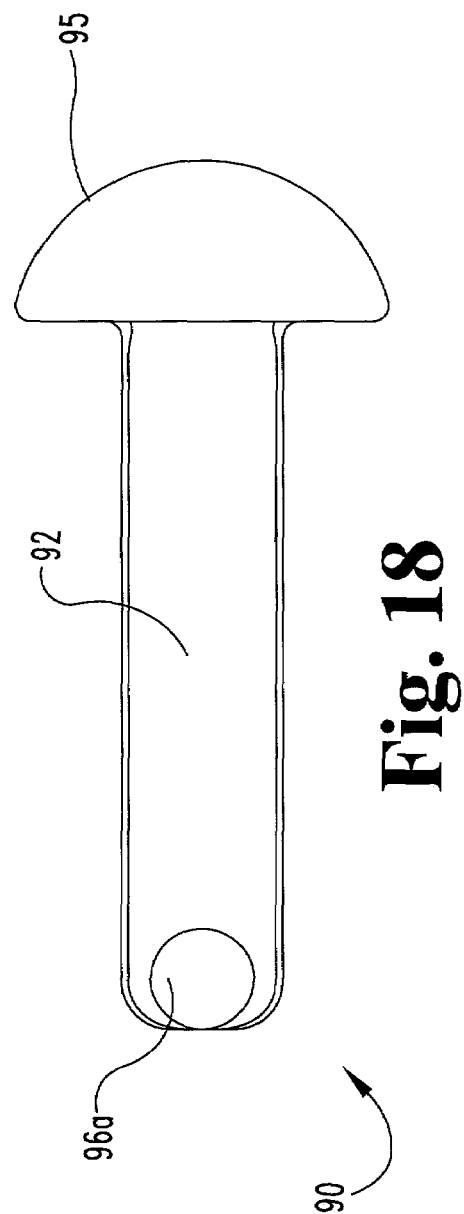
FIG. 18 is an elevation view of a lock pin comprising a portion of the device of FIG. 1.

For the purposes of promoting an understanding of the principles of the invention, reference will now be made to the embodiment illustrated in the drawings and specific language will be used to describe the same. It will nevertheless be understood that no limitation of the scope of the invention is thereby intended. Any such alterations and further modifications in the illustrated device, and any such further applications of the principles of the invention as illustrated therein are contemplated as would normally occur to one skilled in the art to which the invention relates.

The present invention is directed to methods and devices for distracting and/or compressing a portion of the spinal column. The devices can be used in an endoscopic approach to the surgical site, in an open approach to the surgical site, or in procedures using combinations of these approaches. The device can be used in thorascopic, laparoscopic, or other approaches to the spinal column. The device includes a lock member that maintains the compression or distraction force applied by the device without requiring the use of an instrument to maintain the compression or distraction, thus freeing up space in the incision or portal for other instruments.

In one form the device includes a pair of opposite engagement ends each configured for engagement with a corresponding vertebra, a construct engaged to a vertebra, or other device or portion associated with the spinal anatomy. The device includes a mechanism disposed between the opposite engagement ends moveable to vary the distance between the opposite engagement ends in an extend direction and a retract direction. Means for moving the mechanism is provided along with means for locking the mechanism. The means for locking the mechanism has a first position relative to the mechanism to lock the mechanism to prevent movement in one of the extend direction and the retract direction while allowing movement in the other of the extend direction and the retract direction. The means for locking has a second position relative to the mechanism that allows movement in both the extend direction and the retract direction.

In a further form, the device includes a body having a first engagement end and a rack engageable with the body having a second vertebral engagement end opposite the first engagement end. Each of the engagement ends can be configured to engage an anatomical structure of a vertebra or an anchor or other construct engaged to a vertebra or to a portion of the spinal column. The rack can be moved relative to the body with a pinion to move at least one of the vertebral engagement ends towards the other end to impart a compression force. The rack can also be moved relative to the body to move at least one of the engagement ends away from the other end to impart a distraction force. The device includes a locking mechanism that prevents movement of the opposite engagement ends for application of either the compression force or distraction force while allowing movement of the opposite engagement ends for application of the other of the compression force and distraction force. The locking mechanism can be disengaged to allow movement of the opposite engagement ends for application of both compression and distraction forces.

A device 30 according to the invention for providing compression and/or distraction forces is illustrated in FIGS. 1–5. Device 30 includes a mechanism 32 extending between opposite engagement ends 36, 64. Mechanism 32 includes driving means 33 for moving engagement ends 36, 64 in an extension direction E for application of a distraction force and a retraction direction R for application of a compression force. Mechanism 32 includes a locking mechanism 34 having a first position relative to mechanism 32 that prevents the driving means 33 from moving the engagement ends 36, 64 in one of the extension or retraction directions while allowing movement in the other of the extension or retraction directions. Locking mechanism 34 is moveable to a second position relative to mechanism 32 that allows driving means 33 to move engagement ends 36, 64 in both the extension direction and the retraction direction.

Mechanism 32 of device 30 includes a body 35 having first engagement end 36. Mechanism 32 also includes a rack 60 moveably positioned through body 35 that includes second engagement end 64 opposite first engagement end 36. Driving means 33 includes a pinion 80 rotatably coupled to body 35 and in engagement with rack 60 to move rack 60 relative to body 35 in extend direction E and retract direction R. Locking mechanism 34 includes a lock pin 90 moveable between first and second positions to actuate a lock member 100 into and out of engagement with rack 60.

In the illustrated embodiment, first engagement end 36 has a shaft 38 extending from body extension 39 to an enlarged end 37. Enlarged end 37 extends outwardly from shaft 38. Shaft 38 is sized for receipt in the head of an anchor, such as anchor A1 of FIGS. 4–5. Enlarged end 37 and body extension 39 contact respective sides of the anchor to maintain the connection between anchor A1 and body 35 when compression/distraction forces are applied thereto.

As shown in further detail in FIGS. 9–14, body 35 includes a proximal side 48 and an opposite distal side 49. Proximal side 48 is oriented toward the surgeon and distal side 49 toward the patient when device 30 is in position in the patient during surgery (FIG. 5.) It is also contemplated that proximal side 48 and distal side 49 could be oriented laterally or at some angle between lateral/proximal orientations. Body 35 extends between a first end 53 and a second end 54. Body 35 defines a passage 52 extending therethrough which opens at a first end 53 and also at a second end 54. Body 35 further includes an enlarged portion 50 extending between proximal surface 48 and distal surface 49 sized to accommodate a gear bore 55 formed therethrough. Gear bore 55 is in communication with passage 52 as shown in FIG. 11.

Body 35 further includes a lock pin hub 40 extending proximally from proximal side 48. A cutout portion 42 is formed in body 35 in the wall extending along a portion of distal side 49 and the adjacent sidewall that includes enlarged portion 50. A lock member chamber 44 is formed in body 35 in communication with passage 52 and also in communication with cutout portion 42. A camming surface 43 extends along the bottom of chamber 44. Camming surface 43 has a first end adjacent passage 52 and sloping distally toward cutout portion 42. A lock pin bore 56 extends through hub 40 and is in communication with lock member chamber 44. Lock pin hub 40 can be grasped by a surgical tool or the like to assist in positioning device 30 through a cannula or incision to the operative site in the patient. In one specific embodiment, lock pin hub 40 can be grasped by a modified pituitary rongeur that includes a collet mechanism in the working end that allows the surgeon to hold and maneuver device 30 while maintaining locking mechanism 34 in the second, disengaged position.

Referring again to FIGS. 1–5, mechanism 32 of device 30 includes a rack 60 movably disposed within passage 52 of body 35. Referring also to FIGS. 6–8, rack 60 has a first end 62 and opposite second engagement end 64 that is similar to first engagement end 36 of body 35. In the illustrated embodiment, second engagement end 64 has a shaft 65 extending from rack extension 61 to an enlarged end 66. Enlarged end 66 extends outwardly from shaft 65. Shaft 65 is sized for receipt in the head of an anchor, such as anchor A2 of FIGS. 4–5. Enlarged end 66 and rack extension 61 contact respective sides of the anchor to maintain the connection between anchor A2 and rack 60 when compression/distractions forces are applied thereto.

Other configurations for first and second engagement ends 36, 64 are also contemplated. One such configuration is disclosed in U.S. Pat. No. 6,126,660, which is incorporated herein by reference in its entirety. Other configurations could employ, for example, an eyebolt, U-shaped arms defining a slot therebetween, or hook type engagement ends. First and second engagement ends 36, 64 are coupled to anchors A1 and A2, respectively. Anchors A1, A2 can be screws with fixed heads or pivoting, multi-axial heads, bolts, hooks, clamps, rods, plates, interbody device, or other construct engageable to the spinal column. Anchors A1, A2 could also be part of the spinal anatomy, such as the vertebral endplates or spinal processes.

Rack 60 is movable in passage 52 of body 35 in extend direction E and in retract direction R as shown in FIGS. 4–5. Rack 60 is lockable via locking mechanism 34 at any one of a number of positions intermediate a fully retracted position and a fully extended position. One such intermediate position is shown in FIGS. 4–5. Rack 60 defines an engagement surface 68 and an opposite surface 67 extending between first end 62 and engagement end 64 along central axis L. Engagement surface 68 is exposed to gear bore 55 of body 35 when rack 60 is positioned within chamber 52. In the illustrated embodiment, engagement surface 68 includes a number of spaced teeth 69 that are V-shaped defining V-shaped recesses therebetween. A stop member 70 is provided on engagement surface 68 adjacent first end 62.

Referring now to FIGS. 1–5 and 15–17, driving mechanism 33 of device 30 includes a pinion 80 rotatably disposed within gear bore 55. Pinion 80 includes a gear portion 81 having teeth 82 formed therealong and configured to cooperate with teeth 69 of rack 60 to move rack 60 in the retract and extend directions. Pinion 80 is held in gear bore 55 by fastener 88 extending through fastener bore 59 of body 35 (FIG. 11) and into engagement with threaded bore 84 of pinion 80. Fastener 88 rotates along with pinion 80 while holding pinion 80 in gear bore 55. Pinion 80 also includes a head 86 extending therefrom and extending above proximal side 48 of body 35 when pinion 80 is disposed in gear bore 55. Head 86 can have a hex shape or other shape for engagement with a tool to assist in the application of rotary force to pinion 80. Rotation of pinion 80 drives rack 60 in the extend and retract directions.

Figure 19:
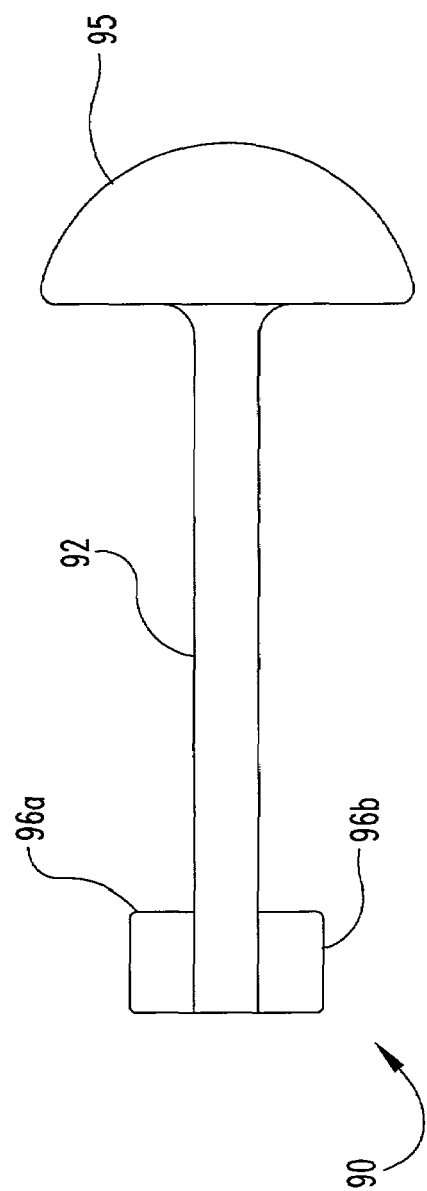
FIG. 19 is an elevation view of the lock pin of FIG. 18 rotated 90 degrees about its longitudinal axis from its FIG. 18 orientation.

FIGS. 18–23 provide further details of locking mechanism 34. Referring to FIGS. 1–5 and 18–19, there is shown a lock pin 90 positionable through lock pin bore 56 of body 35. Lock pin 90 includes a shaft 92 extending from an enlarged head 95. Enlarged head 95 extends proximally from hub 40 when assembled with body 35. Opposite head 95, a pair of cam members 96a, 96b extend laterally from the distal end of shaft 92. Cam members 96a, 96b are engageable with a lock member 100 positioned in lock member chamber 44 of body 35.

Referring now further to FIGS. 20–23, lock member 100 includes a body 102 having teeth 104 formed along an engagement side 108 thereof. When device 30 is assembled, lock member 100 is positioned in lock member chamber 44 with engagement side 108 oriented toward engagement surface 68 of rack 60, and with central axis A extending generally parallel with central axis L of rack 60. Lock member 100 includes a curved end surface 114 extending between a first side surface 112 and a second side surface 116. A proximal surface 110 extends between second side surface 116 and engagement side 108. Curved end surface 114 is oriented toward cutout 42 when lock member 100 is in lock member chamber 44. Body 102 further includes a lock pin receptacle 106 having an engagement surface 118 extending therealong. Receptacle 106 extends from engagement surface 108 through body 102 to second side surface 116.

When positioned in lock member chamber 44, first side surface 112 is in sliding engagement with a lower camming surface 43. Second side surface 116 can be similarly placed in sliding engagement with an upper camming surface 45 along the top of lock member chamber 44. Lock pin 90 extends through lock pin bore 56 with cam members 96a, 96b received in lock pin receptacle 106. Teeth 104 are biased proximally and into engagement with teeth 69 of rack 60 by spring 98 extending between enlarged head 95 of lock pin 90 and hub 40 of body 35.

In order to disengage teeth 104 of lock member 100 from teeth 69 of rack 60, enlarged head 95 is pressed distally to compress spring 98. Cam members 96a, 96b press against and move along engagement surface 118 of lock member 100 away from teeth 104, thereby forcing lock member 100 to move along camming surfaces 43, 45 of chamber 44 toward cutout 42 thereby moving teeth 104 away from and out of engagement with teeth 69 of rack 60. When the compressions force is removed from lock pin 90, spring 98 returns toward its uncompressed condition, thereby moving lock pin 90 and cam members 96a, 96b proximally and drawing lock member 100 proximally along camming surface 43, 45 until teeth 104 engage teeth 69 of rack 60.

In the illustrated embodiment, teeth 104 are engageable with teeth 69 of rack 60 so as to allow movement of rack 60 with pinion 80 in the extension direction E for distraction, but prevent or lock rack 60 from movement in the retraction direction R for compression. Teeth 104 of lock member 100 each include an engaging wall 104a, an advancing wall 104c and a crest 104b extending therebetween. As shown in FIGS. 1 and 7, teeth 69 include a first wall 69a, a second wall 69c and a crest 69c extending therebetween.

When device 30 is assembled and locking mechanism 34 is in its first position, the interdigitation of teeth 104 and teeth 69 allows movement of rack 60 in the extension direction E. As pinion 80 is turned to move rack 60 relative to body 35 in the retraction direction R, engaging walls 104a abut second walls 69c to prevent movement in retraction direction R. In contrast, when it is desired to move rack 60 with respect to body 35 with pinion 80 in the extension direction E to apply a distraction force, the advancing walls 104c ride over first wall 69a and crest 69b until teeth 104 interdigitate in the next adjacent teeth 69. Engaging walls 104a of teeth 104 engage respective ones of the second walls 69c of the next adjacent teeth 69 to maintain the applied distraction force and prevent movement in the retraction direction R. When locking assembly 34 is in its second position, lock pin 90 is pressed to disengage lock member 100 from teeth 69, and movement of rack 60 relative to body 35 in both the extension direction E and retraction direction R is possible.

It is further contemplated that the positions of engaging walls 104a and advancing walls 104c along teeth 104 could be reversed so that, when lock pin 90 and lock member 100 are in their normally engaged position, rack 60 could be moved relative to body 35 in the retraction direction R but is locked against movement in the extension direction E. In another form, it is contemplated that lock member 100 include teeth 104 with engaging walls 104a along each side of each tooth 104 so that movement in both the extension direction E and the retraction direction R is prevented unless locking mechanism 34 is in its second position. In yet a further form, the teeth along lock member 100 are identical to the teeth along rack 60 to prevent movement in either the extend direction or retract direction.

In one specific embodiment, engaging wall 104a is sloped at an angle B with respect to axis A of lock member 100, and advancing wall 104c is sloped at an angle C with respect to axis A of lock member 100. Crest 104b extends parallel with axis A, and teeth 104 and teeth 69 have the same pitch along their respective axes A and L. Teeth 69 have walls 69a, 69c that each form angle D with axis L of rack 60. Engaging wall 104a has a slope greater than that of the adjacent wall 69c of teeth 69 to abut the respective wall 69c when driving mechanism 33 is manipulated to move opposite ends 36, 64 in the retraction direction R. Advancing wall 104c has a slope that is less than that of the adjacent wall 69a of teeth 69 so that advancing wall 104c can ride over crest 69c when driving mechanism 33 is manipulated to move opposite ends 36, 64 in the extension direction E. In one specific embodiment, angle B is about 85 degrees, angle C is between about 35 to 40 degrees, and angle D is about 65 degrees.

Device 30 also includes means for limiting translation of rack 60 within passage 52. Rack 60 is movable within chamber 52 between a fully retracted position and a fully extended position. In the illustrated embodiment, the limiting means includes a stop member 70 embedded in engagement surface 68 between teeth 69 of rack 60. Stop member 70 is in the form of a pin press fit into to engagement surface 69. Stop member 70 interferes with teeth 82 of pinion 80 to prevent teeth 82 from interdigitating with teeth 69 of rack 60 at the location of stop member 70, thus limiting the translation of rack 60 in body 35. Stop member 70 can be located toward the proximal edge of engagement surface 69 away from the portion of engagement surface 69 engaged by lock member 100 so as to not interfere with function of lock member 100 when it is positioned adjacent thereto.

Device 10 can be provided with other features to enhance and facilitate its use in surgical procedures. For example, the outer surface of rack 60 can be provided indicia for measuring a distance between the vertebral engagement ends of body 35 or to provide and indication of distraction/compression distance. Such indicia could be viewed endoscopically, microscopically, directly or otherwise by the surgeon.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A device for applying a force to a spinal column segment, comprising:
   a pair of opposite engagement ends each configured for engagement with a portion of the spinal column segment;
   a mechanism disposed between said pair of opposite engagement ends moveable to vary the distance between said engagement ends;
   means for moving said mechanism in an extend direction to apply a distraction force and in a retract direction to apply a compression force; and
   means for locking said mechanism having a first position in engagement with said mechanism such that said mechanism is not movable in one of said extend direction and said retract direction and is movable in the other one of said extend direction and said retract direction, said means for locking having a second position allowing said mechanism to be moved in both said extend direction and said retract direction.

2. The device of claim 1, wherein each of said pair of opposite engagement ends is coupled to an anchor engaged to a vertebra.

3. The device of claim 1, wherein said mechanism includes:
   a body integral with one of said pair of opposite engagement ends, said body defining a passage therethrough and a bore intersecting said passage; and
   a rack movably received in said passage, said rack integral with the other of said pair of opposite engagement ends and having a plurality of teeth formed therealong.

4. The device of claim 3, wherein said means for moving said mechanism includes a pinion rotatably received in said bore in engagement with said rack.

5. The device of claim 4, wherein said pinion includes a number of teeth therearound that interdigitate with selective ones of said plurality of teeth of said rack.

6. The device of claim 3, wherein said means for locking is spring biased to said first position.

7. The device of claim 3, wherein said means for locking includes:
   a lock member movably mourned in a chamber of said body and engageable with said rack; and
   a lock pin engaged to said lock member and extending therefrom through said body, said lock pin engageable to move said lock member from said first position to said second position.

8. The device of claim 7, wherein said lock member is movable along at least one camming surface in said chamber between said first position and said second position.

9. The device of claim 7, wherein said lock pin has a cam member extending from a distal end thereof and said lock member defines a receptacle sized to receive said cam member.

10. The device of claim 9, wherein said cam member moves in said receptacle as said lock member is moved between said first position and said second position.

11. The device of claim 7, wherein said lock member includes a number of teeth engageable with said plurality of teeth of said rack, at least one of said number of teeth having an engaging wall and an advancing wall, said engaging wall of said at least one of said number of teeth of said lock member engaging at least one of said plurality of teeth of said rack such that said mechanism is not moveable in one of said extend direction and said retract direction, said advancing wall engaging said at least one of said plurality of teeth of said rack such that said mechanism is moveable in the other one of said extend direction and said retract direction.

12. The device of claim 11, wherein said mechanism has a central axis extending in the extend and retract directions, said engaging wall has a slope relative to said central axis that is greater than a slope relative to said central axis defined by walls of said at least one of said plurality of teeth of said rack.

13. The device of claim 12, wherein said advancing wall has a slope relative to said central axis that is less than the slope relative to said central axis defined by walls of said at least one of said plurality of teeth of said rack.

14. The device of claim 1, wherein each of said pair of engagement ends includes a shaft extending generally in the extend and retract directions and an enlarged end extending from said shaft.

15. A device for applying a force to a spinal column segment, comprising:
   a body having a first engagement end, said body defining a passage therethrough and a bore intersecting said passage; and
   a rack movably received in said passage, said rack having a second engagement end opposite said first engagement end;
   a pinion rotatably received in said bore and in operative engagement with said rack to move said first and second engagement ends in an extend direction and a retract direction; and
   a locking mechanism mounted to said body, said locking mechanism having a first position in engagement with said rack locking said first and second engagement end from movement in one of said extend direction and said retract direction while allowing said first and second engagement ends to be moved in the other one of said extend direction and said retract direction, said locking mechanism having a second position allowing said first and second engagement ends to be moved in both said extend direction and said retract direction.

16. The device of claim 15, wherein each of said first and second engagement ends is coupled to an anchor engaged to a vertebra.

17. The device of claim 16, wherein each of said pair of engagement ends includes a shaft extending generally in the extend and retract directions and an enlarged end extending from said shaft.

18. The device of claim 15, wherein said pinion includes a number of teeth that interdigitate with selective ones of a plurality of teeth formed along said rack.

19. The device of claim 15, wherein said locking mechanism includes a lock member spring biased to said first position.

20. The device of claim 19, wherein said lock member is movably mounted in a chamber of said body in engagement with said rack, said locking mechanism including:
a lock pin engaged to said lock member and extending therefrom through said body, said lock pin engageable to move said lock member from said first position to said second position.

21. The device of claim 20, wherein said lock member is movable along at least one camming surface in said chamber between said first position and said second position.

22. The device of claim 20, wherein said lock pin has a cam member extending from a distal end thereof, said lock member defining a receptacle sized to receive said cam member.

23. The device of claim 22, wherein said cam member moves in said receptacle as said lock member is moved between said first position and said second position.

24. The device of claim 20, wherein said lock member includes a number of teeth engageable with said plurality of teeth of said rack, at least one of said number of teeth having an engaging wall and an advancing wall, said engaging wall of said at least one of said number of teeth of said lock member engaging at least one of said plurality of teeth of said rack such that said mechanism is not moveable in one of said extend direction and said retract direction, said advancing wall engaging said at least one of said plurality of teeth of said rack such that said mechanism is moveable in the other one of said extend direction and said retract direction.

25. The device of claim 24, wherein said mechanism has a central axis extending in the extend and retract directions, said engaging wall has a slope relative to said central axis that is greater than a slope relative to said central axis defined by walls of said at least one of said plurality of teeth of said rack.

26. The device of claim 25, wherein said advancing wall has a slope relative to said central axis that is less than the slope relative to said central axis defined by walls of said at least one of said plurality of teeth of said rack.

27. A device for applying a force to a spinal column segment, comprising:
a body having a first end member, said body defining a passage therethrough and a chamber in communication with said passage;
a rack moveably received in said passage, said rack having a second end member opposite said first end member;
a driving mechanism in operative engagement with said rack to move said first and second end members in an extend direction for application of a distraction force and in a retract direction for application of a compression force; and
a lock member positioned in said chamber of said body, said lock member having a lock pin engaged thereto engageable to move said lock member between a first position wherein said lock member engages said rack and a second position wherein said lock member is not engaged with said rack, wherein:
in said first position said lock member prevents said first and second end members from being moved in one of said extend direction and said retract direction and allows said first and second end members to be moved in the other of said extend direction and said retract direction; and
in said second position said first and second end members are moveable in both said extend direction and said retract direction.

28. The device of claim 27, wherein said lock member is spring biased to said first position.

29. The device of claim 28, further comprising a spring between said body and said lock pin to spring bias said lock member to said first position.

30. The device of claim 27, wherein said body includes a bore in communication with said passage and said drive mechanism includes a pinion in said bore having a number of teeth that interdigitate with teeth formed along said rack.

31. The device of claim 27, wherein said lock member includes at least one tooth engageable with said rack to prevent said rack from being moved in one of the extend direction and the refract direction.

32. The device of claim 27, wherein said lock member includes an engagement surface and said lock pin includes a cam member engageable with said engagement surface to move said lock member between said first position and said second position.

33. The device of claim 32, wherein said cam member is slidable along said engagement surface.

34. The device of claim 27, wherein said lock member includes a number of teeth engageable with at least one of a plurality of teeth along said rack, at least one of said number of teeth having an engaging wall and an advancing wall, said engaging wall of said at least one of said number of teeth of said lock member engaging at least one of said plurality of teeth of said rack so that said mechanism is not moveable in one of said extend direction and said retract direction, said advancing wall engaging said at least one of said plurality of teeth of said rack so that said mechanism is moveable in the other one of said extend direction and said retract direction.

35. The device of claim 34, wherein said rack has a central axis extending in the extend and retract directions, said engaging wall has a slope relative to said central axis that is greater than a slope relative to said central axis defined by walls of said at least one of said plurality of teeth of said rack.

36. The device of claim 35, wherein said advancing wall has a slope relative to said central axis that is less than the slope relative to said central axis defined by walls of said at least one of said plurality of teeth of said rack.

37. The device of claim 27, wherein:
in said first position said lock member prevents said first and second end members from being moved in either of said extend direction and said retract direction; and
in said second position said first and second end members are moveable in both said extend direction and said retract direction.

38. A device for applying a force to a spinal column segment, comprising:
- a pair of opposite engagement ends each configured for engagement with a portion of the spinal column segment;
- a mechanism disposed between said pair of opposite engagement ends moveable to vary the distance between said engagement ends;
- a driving mechanism operable to move said opposite ends in an extend direction to apply a distraction force and in a retract direction to apply a compression force; and
- a locking mechanism having a first position in engagement with said mechanism such that said opposite ends are not movable in one of said extend direction and said retract direction and is movable in the other one of said extend direction and said retract direction, said locking mechanism having a second position allowing said mechanism to be moved in both said extend direction and said retract direction.

39. The device of claim 38, wherein said mechanism includes:
- a body integral with one of said pair of opposite engagement ends, said body defining a passage therethrough and a bore intersecting said passage; and
- a rank movably received in said passage, said rack integral with the other of said pair of opposite engagement ends and having a plurality of teeth formed therealong.

40. The device of claim 39, wherein said driving mechanism includes a pinion rotatably received in said bore in engagement with said rack.

41. The device of claim 39, wherein said locking mechanism includes:
- a lock member movably mounted in a chamber of said body and engageable with said rack; and
- a lock pin engaged to said lock member and extending therefrom through said body, said lock pin engageable to move said lock member from said first position to said second position.

* * * * *

UNITED STATES PATENT AND TRADEMARK OFFICE
CERTIFICATE OF CORRECTION

| | | |
|---|---|---|
| PATENT NO. | : 7,011,658 B2 | Page 1 of 1 |
| APPLICATION NO. | : 10/092961 | |
| DATED | : March 14, 2006 | |
| INVENTOR(S) | : John Stewart Young | |

It is certified that error appears in the above-identified patent and that said Letters Patent is hereby corrected as shown below:

Col. 12, claim 39, line 6, replace "rank" with --rack--.

Signed and Sealed this

Eighteenth Day of September, 2007

JON W. DUDAS
*Director of the United States Patent and Trademark Office*